United States Patent [19]

Sanchez et al.

[11] 4,437,967
[45] Mar. 20, 1984

[54] APPARATUS FOR ELECTROPHORETICALLY FRACTIONATING A SOLUTION

[75] Inventors: Victor Sanchez, Ramonville-Saint-Agne; Patrick Espenan, Toulouse; Ernest Casademont, Montgiscard; J. Pierre Lafaille, Saint-Orens, all of France

[73] Assignee: Centre National De La Recherche Scientifique, Paris, France

[21] Appl. No.: 319,408

[22] Filed: Nov. 9, 1981

[30] Foreign Application Priority Data

Nov. 7, 1980 [FR] France ................................ 80 23952

[51] Int. Cl.$^3$ ............................................ B01D 13/02
[52] U.S. Cl. .................................. 204/301; 204/180 P
[58] Field of Search ............................ 204/301, 180 P

[56] References Cited

U.S. PATENT DOCUMENTS

| | | | |
|---|---|---|---|
| 3,073,774 | 1/1963 | Roberts et al. | 204/301 |
| 3,359,196 | 12/1967 | Chen | 204/301 |
| 3,933,617 | 1/1976 | Yamamoto et al. | 204/301 |
| 4,350,581 | 9/1982 | Schmoldt et al. | 204/301 |

FOREIGN PATENT DOCUMENTS

| | | | |
|---|---|---|---|
| 586187 | 11/1959 | Canada | 204/301 |
| 750350 | 1/1967 | Canada | 204/301 |
| 827350 | 12/1951 | Fed. Rep. of Germany | 204/301 |

*Primary Examiner*—R. L. Andrews
*Assistant Examiner*—Terryence Chapman
*Attorney, Agent, or Firm*—Shlesinger, Arkwright, Garvey & Fado

[57] ABSTRACT

The fractionating apparatus of the invention for the separation of at least two dissolved groups of substances in a solution is of the type wherein an electric field is applied in fractionating chambers separated by semipermeable membranes so as to generate different migrations by various groups of substances; each fractionating chamber is bounded by a peripheral frame 3 provided with a plurality of strips 23; the two semi-permeable membranes 1 and 2 of the chamber are applied on either side against the faces of said frame and against the faces of said strips; spacer compartments are advantageously provided on either side of the fractionating chambers, said spacer compartments containing an auxiliary solution capable of enhancing by high rate ion exchanges the differences in migrations of the substances to be separated.

10 Claims, 15 Drawing Figures

APPARATUS FOR ELECTROPHORETICALLY FRACTIONATING A SOLUTION

The invention concerns a device for fractionating a solution in order to separate at least two groups of substances dissolved in it; it relates to an electrophoretically fractionating apparatus using an electric field to generate a migration of the substances.

Electrophoresis already has been used in the laboratory to fractionate a solution and to obtain liquid fractions enriched in substances contained in the initial solution; the main significance of this type of process is that it preserves the specific properties of the fractionated substances without denaturing them and also in that it draws only low electric power. Several embodiments of apparatus implementing such electrophoretic process will be found in particular in the French Pat. No. 2,131,859 or the U.S. Pat. Nos. 2,801,962; 2,878,178; 3,989,613 and 936,805.

However such apparatus only offer relatively mediocre efficiency, the periods of operation required to achieve a given fractionation often being very long.

Thus in practice the known apparatus does not allow making full use of the advantages offered by the electrophoretic processes (low power consumption, lack of denaturation of the fractionated substances) due to the defects inherent in each apparatus, which run against industrial implementation. Moreover, as regards most of the known fractionating equipment, the initial solution which must be diluted and dialyzed requires a prior preparation, as a rule to adjust its pH, in order to make possible efficient fractionating. These dialysis operations are lengthy and delicate and are sources of bacterial contaminations of the solutions.

It is the object of the present invention to eliminate the defects of known electrophoretic fractionating apparatus in order to make full use of the advantages offered by electrophoresis.

As essential object of the invention is to substantially improve the efficiency of the apparatus so as to obtain high fractionating rates in short periods of operation and compatible with implementation on an industrial scale.

Another object is to offer an apparatus which can be manufactured at low cost.

Another object is to allow continuous fractionation.

Another object is to extend the possible applications of the electrophoretic fractionation processes on account of the substantial improvement in the efficiency of the apparatus of the invention.

Another object is to radially eliminate any prior dialysis stage or any other similar type preparation.

To that end the apparatus for the electrophoretic fractionation of the invention is of the type comprising electrodes to generate an electric field between them, at least two semi-permeable membranes bounding at least one fractionating chamber provided with solution intake means and evacuation means for the liquid fractions; in the present invention, each fractionating chamber is bounded by a peripheral frame provided with a plurality of strips joining two sides of said frame and of the same thickness as this frame, the two semi-permeable membranes being applied on either side against the faces of said frame and against the faces of said strips so that these membranes are kept apart by a constant distance and so that the volume included between said membranes be divided by the strips into a plurality of elongated volumes.

Experiments has shown that the fractionating efficiency is much raised in the apparatus of the invention, essentially for the following reasons:

the apparatus structure allows limiting the dead zones in each fractionating chamber by channeling the flow in relatively narrow volumes;

this structure also makes it possible to ensure a laminar flow in the chamber and thusly to avert remixing the separated substances (such as is caused in the known equipment by turbulences);

lastly this structure ensures fixation of the membranes accross their entire surface and allows bringing them near one another at a small gap regardless of the zones affected.

As will be better understood further below, the last effect is essential in practice, as not only it determines a better exchange between the neighboring fractionating chambers but also and more importantly it makes it possible to substantially increase the efficiency within each chamber; here experiment has shown that for given substances and for given intake and evacuation rates, the curve providing the variations in the fractionating efficiency (i.e., the separation factor) has a sharp maximum at a specific chamber thickness; for instance in the case of an initial solution containing albumin which is fractionated to obtain a fraction enriched in this substance, the maximum value of the separation factor is obtained within a range of thickness essentially between 0.15 and 0.40 cm as a function of the expected flow rates.

Thanks to the perfect guidance of the membranes along their surface, the structure of the apparatus of the invention allows adjusting in a very accurate manner the distance between these membranes (and hence the thickness of the fractionating chambers), so as to be in each case within the range of separation maximum.

Moreover, in another characteristic of the invention combined with those already described, spacer compartments are arranged between each electrode and the corresponding end fractionating chamber; these compartments are associated with means feeding an auxiliary solution and with means for evacuating it. They are bounded by a frame provided with strips similar to those already mentioned, the membrane of the electrode compartment resting against one face of said frame and one face of said strips while the membrane of the end fractionating chamber rests against the other face of said frame and the other face of said strips. The strips of said frame are arranged opposite the strips of the frames of the fractionating chambers for the purpose of forming longitudinal volumes located opposite the corresponding volumes of said chambers.

Thus, in such an apparatus, the electric field for fractionating also serves to generate rapid ion exchanges across the membranes between the initial solution contained in the various fractionating chambers and the auxiliary solution contained in the spacer compartments. In this manner the prior preparation operations required in certain conventional equipment are radically eliminated, in particular regarding dialysis, and so are furthermore all the attendant drawbacks; furthermore, the initial solution no longer requires being diluted and the process can be applied to natural solutions in the state in which they are produced or collected. For instance the process can be directly applied to blood serum or plasma, so that all the handling and the precautions required by the dilution stage are eliminated.

The essential characteristics of the initial solution that determine the differences in migration between the substances consist of its pH and its saline concentration. As a consequence, the concentration and the nature of the ions of the auxiliary solution are so selected in each application as to obtain ion exchanges capable of setting a pH and a saline concentration adapted to the initial solution. This selection depends on the substances in mutual presence and can be carried out after completion of prior tests using several auxiliary solutions containing different types of ions at different solutions and different pH's. For instance the following ions can be used: phosphate ($Na_2HPO_4$, $KH_2PO_4$, $K_2HPO_4$, $NaH_2PO_4$ ...) ions, carbonate ions, barbitone ions, acetate ions etc.

The apparatus of the invention makes it possible to perform continuously the electrophoretic process by means of a continuous intake of the initial solution and continuous evacuation of the liquid fractions and by generating a circulation of the auxiliary solution at the rear of the corresponding semi-permeable membrane(s) so as to renew continuously said solution for the purpose of maintaining an essentially constant ion concentration in said solution.

The invention was outlined above and other features, purposes and advantages will become clear in relation to the description to follow which provides in relation to the attached drawings on one hand a preferred embodiment of the apparatus of the invention and on the other hand examples of electrophoresis implemented by means of said apparatus; these drawings are in integral part of the description.

Figure 14:
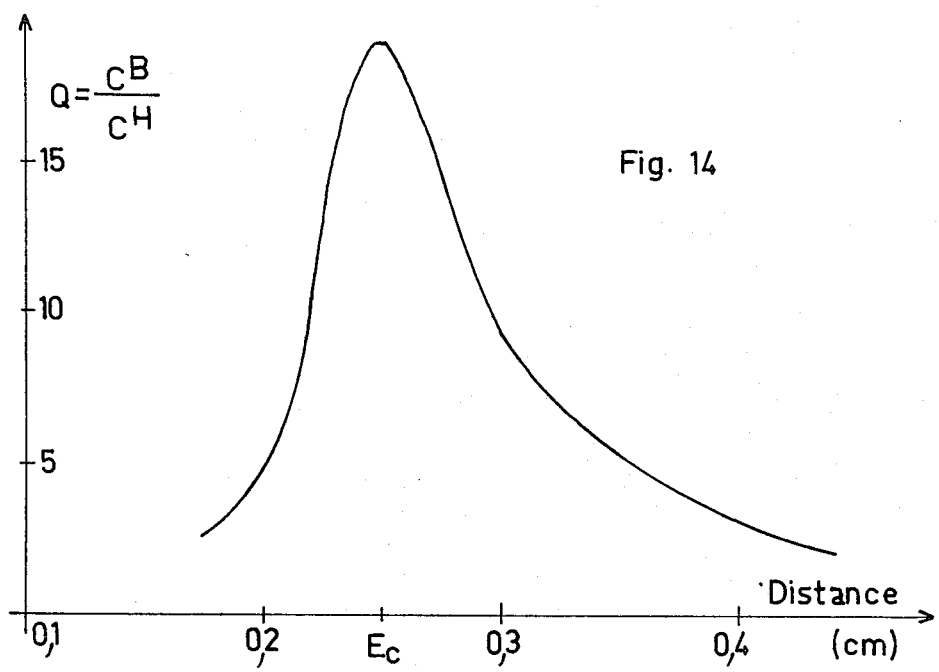
Figure 15:
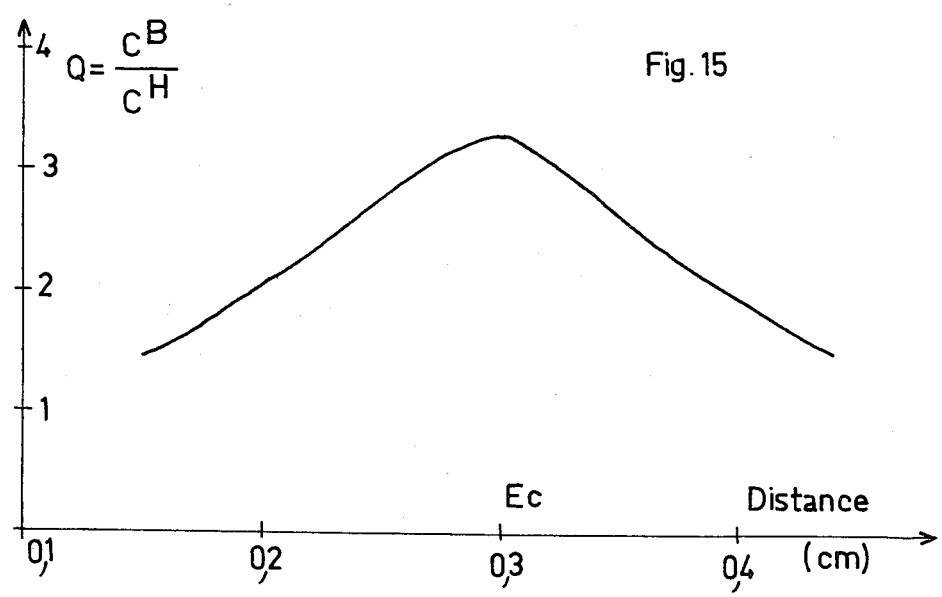

FIGS. 8 through 13 are analytical spectra illustrating the results of implementation 1 through 5;

FIGS. 14 and 15 are the curves showing the separation factor as a function of the fractionating-chamber thickness of the examples 6 and 7.

The apparatus illustratively shown in FIGS. 1 through 7 comprises several abutting fractionating chambers $C_1$, $C_2$, $C_3$ for holding the initial solution which must be fractionated, two spacer compartments $G_1$, $G_2$ located on either side of the two end chambers and for the purpose of holding an auxiliary solution, and two electrode compartments $E_1$, $E_2$ located on either side of the spacer compartments and for holding an ion solution.

Each fractionating chamber $C_1$, $C_2$, $C_3$ is bounded on its two large sides by two membranes such as 1 and 2 (FIGS. 2, 3, 4, 5) which are common to the two neighboring chambers and partition them. Moreover each chamber is bounded at its periphery by a frame 3 against which the membranes 1 and 2 are hermetically applied. These frames will be described in detail further below.

Similarly each spacer compartment $G_1$ or $G_2$ is kept apart on one hand from the adjacent fractionating chamber by a semi-permeable membrane 4 identical with those separating the chambers and on the other hand from the adjacent electrode compartment by an identical semi-permeable membrane 5; further, each spacer compartment is bounded to its periphery by a frame 6 against which the membranes 4 and 5 are hermetically applied; these frames are described in detail further below.

Each electrode compartment $E_1$ or $E_2$ is bounded on its large faces by the membrane 5 separating it from the spacer compartment and by a lateral panel 7 comprising on its inside face a conducting layer 8 constituting the electrode and connected to an electric source. At its periphery each electrode compartment is bounded by a frame 9 similar to the frame 6 of the spacer compartment (except for the feed and evacuation apertures, which are lacking in this case).

In the example, the membranes, frames and lateral panels are rectangular and constitute a stack guided by rods such as 10 and kept compressed by plates 11 and 12. One of the plates 12 is fixed to a support 13 while the other plate 11 is movable and associated with a manual conventional clamping means 14 which compresses the plates to ensure the hermeticity of the stack.

Figure 1:
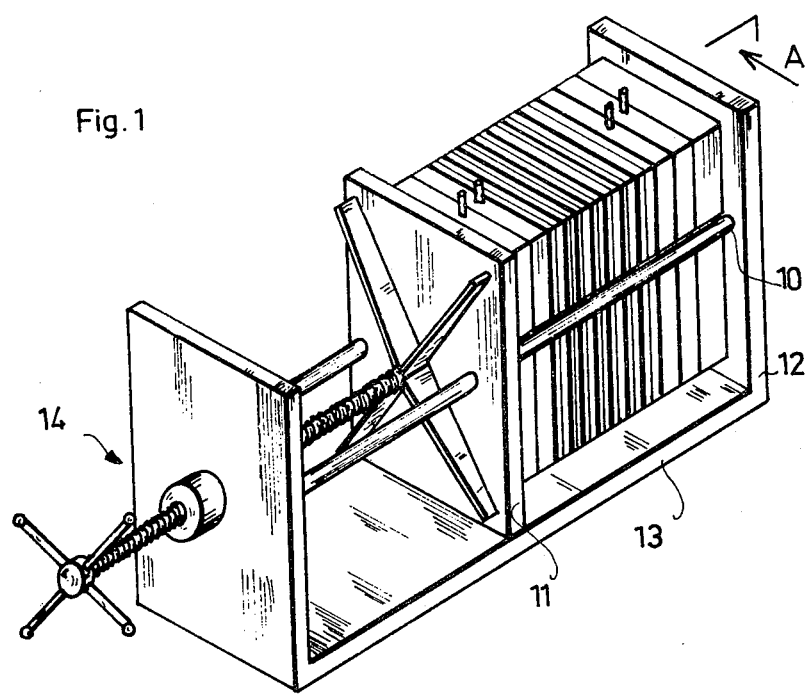
FIG. 1 is a perspective of an apparatus of the invention.
Figure 2:
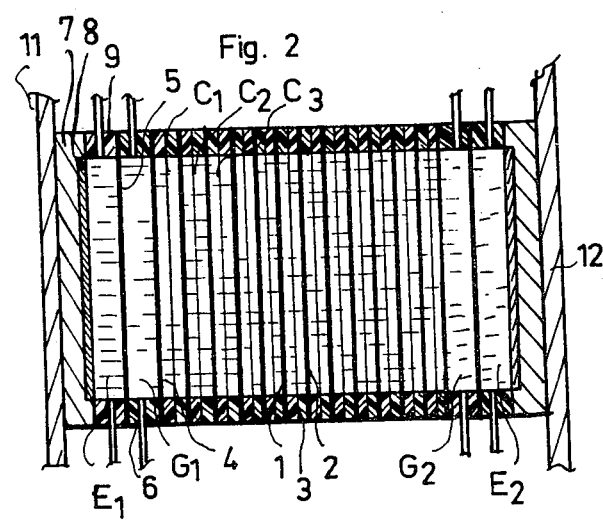
FIG. 2 is a partial sectional view in a vertical plane A.
Figure 3:
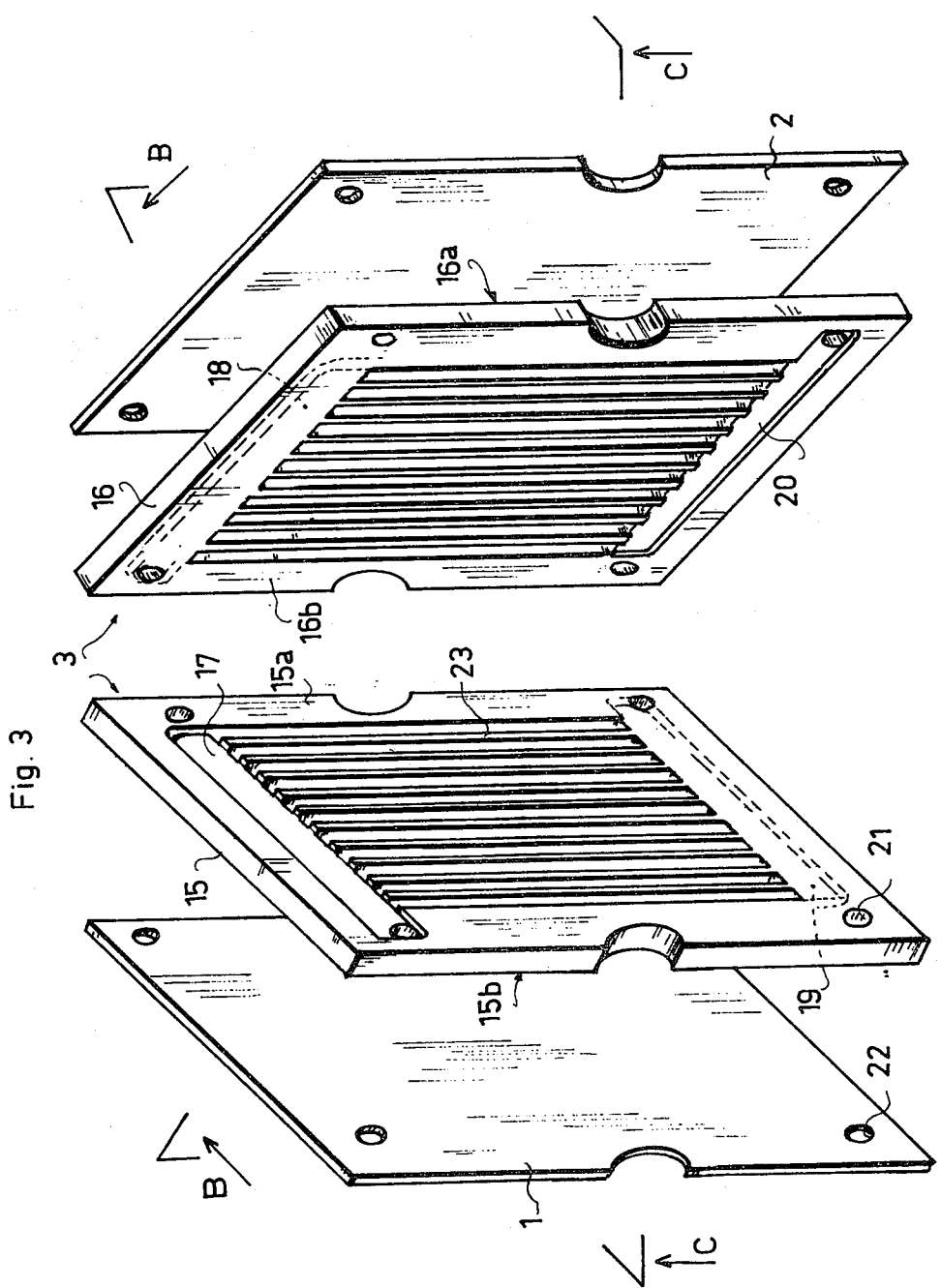
FIG. 3 is a schematic perspective of the constituting elements bounding a fractionating chamber and shown apart from each for better clarity.
Figure 4:
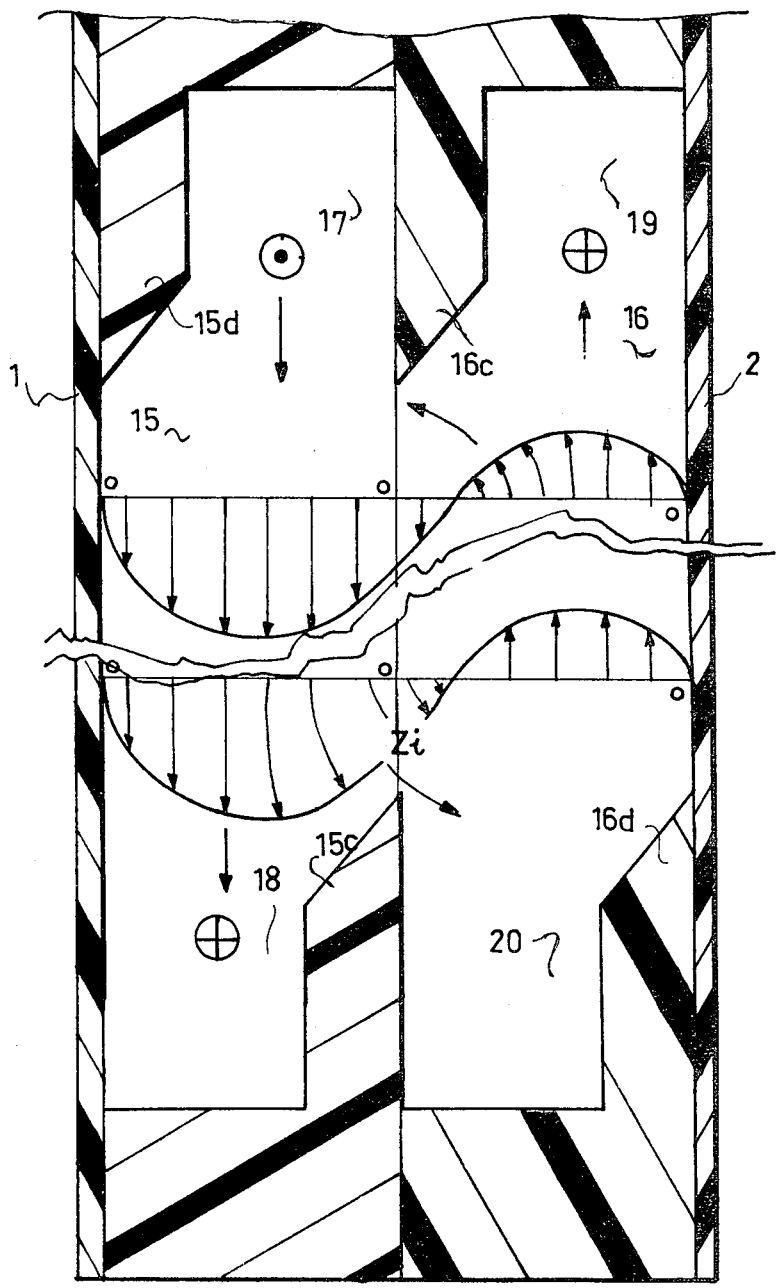
FIG. 4 is a section on a much enlarged scale of this chamber in the operative state, the section passing through a vertical plane BB, with a symbolic diagram of the convection speeds plot.
Figure 5:
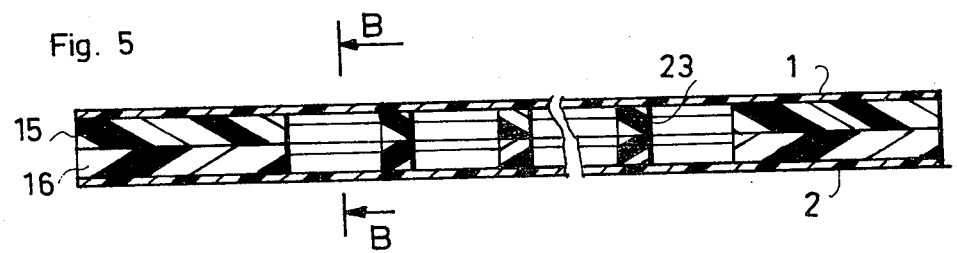
FIG. 5 is a section through said chamber in a horizontal plane CC.

As shown in FIGS. 3, 4 and 5, the frame 3 of each fractionating chamber $C_1$, $C_2$ consists of two identical panels 15, 16 hermetically abutting one another by their faces 15a, 16b; the semi-permeable membranes 1 and 2 separating the chamber under consideration from the adjacent chambers are pressed against the other faces 15b, 16a of said panels. The thickness of each of these panels equals half that of the frame (hence it is equal to half the chamber thickness). These panels may be made of the dielectric material which is inert with respect to the initial solution to be treated, for instance they may be made of methyl polymethacrylate.

Each panel 15 or 16 on one of its faces 15a or 16a comprises a clearance 17 or 18 extending along one side (for instance the upper side in FIG. 3); each panel comprises on its opposite face 15b or 16b an identical clearance 19 or 20 extending along the opposite side (lower edge).

One of these clearances, for instance 17 assumes the function of the intake conduit for the initial solution to feed it to the active zone of the chamber, while two other clearances, for instances 18 and 19, will act as a discharge conduits (one clearance, 20, is not used in the example).

Furthermore, the panels 15 and 16 that form each frame are each bored through by four aligned apertures such as 21. The upper clearance of each panel (17 or 18) extends as far as one of these apertures 21 without however communicating with the other aperture, whereas the lower clearance (19 or 20) extends as far as the aperture located at the other side without communicating with the other aperture.

These apertures will allow parallel feeding of the initial solution to the intake conduits of the various chambers (said conduits being formed by the clearances 17) and to evacuate the liquid fractions from their evacuation conduits (formed by the clearances 18 and 19). To make possible this feeding or evacuation, each semi-permeable membrane also is perforated by four apertures such as 22 aligned with the apertures 21.

Moreover, each of the panels 15 or 16 forming one frame 3 of a fractionating chamber is provided with parallel strips such as 23 extending vertically from one side of the frame to the other as far as its clearances; these strips 23 thusly divide the volume between these clearances into a plurality of elongated volumes constituting the active zone of the chamber. They permit dividing the stream of the initial solution into a plurality of parallel streamlets extending between the two membranes 1 and 2 of the chamber under consideration: the intake of the initial solution toward said streamlets and the evacuation of the liquid fractions from them are carried out in parallel by channel means formed by the upper and lower clearances.

Such design offers the advantage of limiting the dead zones in the chamber, of channeling the flow into relatively narrow volumes, whereby the fractionating effectiveness is increased. Further, the semi-permeable membranes rests against the faces of the strips 23 and are very well kept in place without there being a significant risk of deformation, so that they can be arranged at very precise spacings from one another, such distances possibly being very small (practically about 0.2 to 0.3 cm for maximum separation efficiency, as shown below).

Moreover and as clearly shown in FIG. 4, which is a cross-section of a chamber at one of the streamlets (section through a plane BB perpendicular to the frame), the panels 15 and 16 constituting each frame constitute partition elements 15c and 16c at each liquid streamlet along the two sides of the frame.

One partition element 16c separates the upper intake conduit formed by the clearance 17 of the upper evacuation conduit formed by the clearance 19, while the other partition element 15c defines the lower evacuation conduit formed by the clearance 18.

In the example, the partition elements 15c, 16c are bevel-shaped as shown in FIG. 4 and point from the withdrawal zones 18 and 19 to an intermediary zone Zi of the chamber where the convection rate is very low; (the FIG. 4 symbolically shows the plot of the convection rates inside a liquid streamlet).

Be it noted also that a divergent diffusion element 15d identical in structure with the partition elements 15c or 16c is formed by the panel 15 to achieve a divergent intake of the initial solution. As the panels 15 and 16 are identical, the panel 16 comprises a similar element 16d at the rim of its clearance 20 (which is without any function in the example being described because no evacuation at all takes place through this clearance 20).

The designs described above allow manufacturing very economically a frame 3 by means of two identical panels (which are merely abutted one against the other after reversal and turning upside down from their superposed arrangements), thereby providing each chamber with a maximum fractionating rate (all other factors being equal) due to the precise control of the chamber thickness, the reduction in remixing between the separated fractions and the initial solutions, the absence of deformations in the smei-permeable and the limitation of the dead zones.

Figure 6:
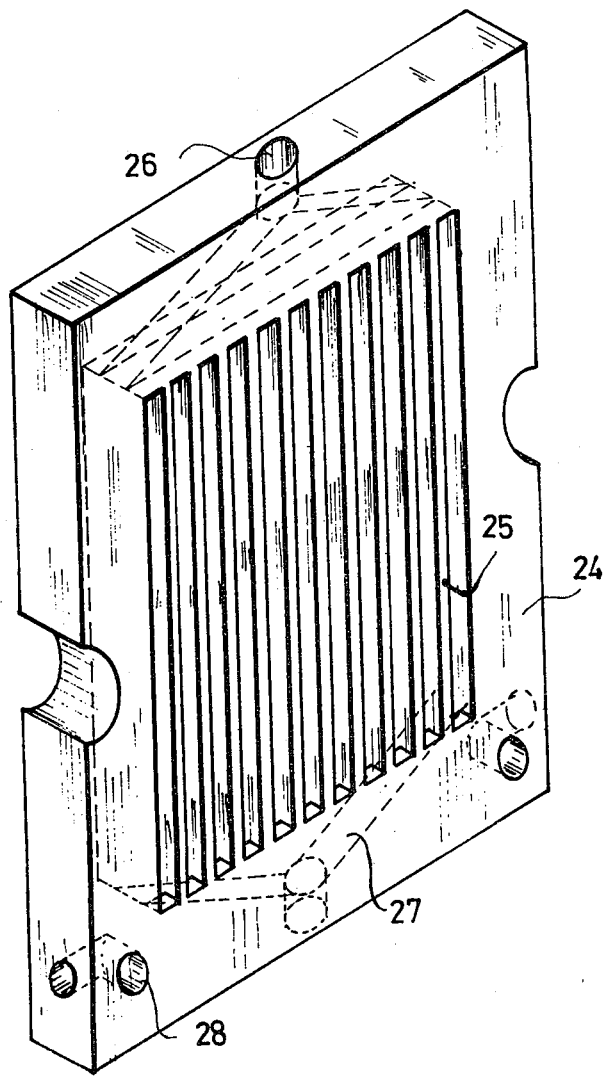
FIG. 6 is a perspective of a frame forming a clearance compartment.

Elsewhere, FIG. 6 shows a frame 24 defining each spacer compartment $G_1$ and $G_2$. This frame comprises strips 25 extending vertically from one side to the other of this frame opposite the strips 23 of the frames 3 of the fractionating chambers; these strips 25 thus define elongated volumes opposite the active chamber volumes.

The frame 24 furthermore is perforated by feed means 27 to supply in parallel these elongated volumes with auxiliary solution and by evacuation means 26 to evacuate in parallel the auxiliary solution following its circulation in said volumes.

Furthermore, it is perforated by two elbow orifices such as 28; as regards the frame of one of the spacer compartments ($G_1$), one of these orifices is aligned with and communicates with the initial-solution feed apertures (21, 22) of the frames and membranes of the fractionating chambers for the purpose of feeding the intake conduits of said chambers while the other elbow orifice 28 is aligned and communicates with the evacuation apertures to collect a liquid fraction; as regards the frame of the other spacer compartment ($G_2$), which is inverted in position with respect to the first frame, one of these orifices is aligned and communicates with the evacuation apertures of the other liquid fraction.

The frame arranged in each electrode compartment $E_1$, $E_2$ is similar to the above described frame 24 except for the orifices 28 which are absent. It makes it possible to circulate an ion solution, eliminating the products formed at the electrode contacts, and to confine the generated electric field only to the active zones of the fractionating chambers and to the spacer compartments (said zones being between the strips).

Figure 7:
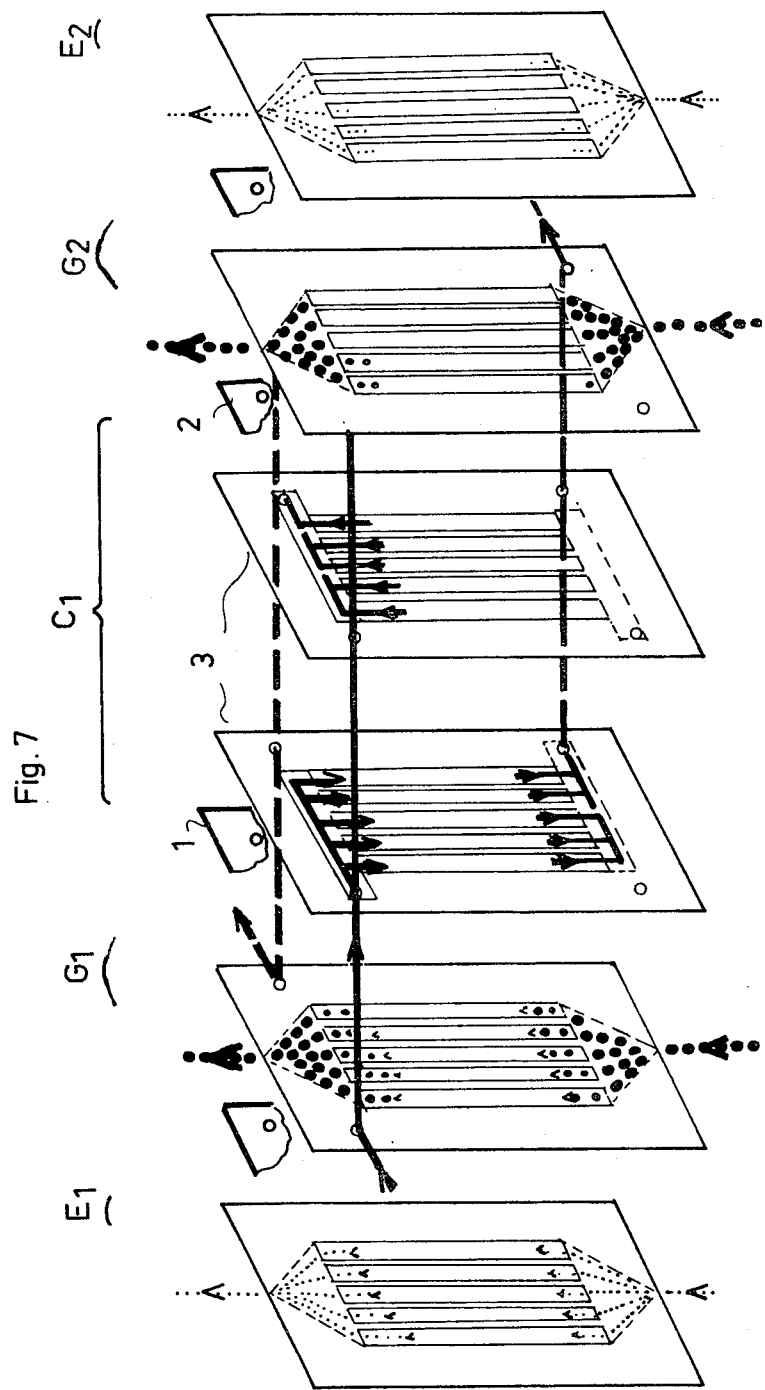
FIG. 7 is an exploded schematic showing the liquid circulation in the apparatus.

FIG. 7 is a schematic of the circulation of the various liquids, showing only one fractionating chamber, and also showing again the circulation paths of the following:

initial solution (solid phase)

two separated liquid fractions (dash lines)

auxiliary solutions in the two spacer compartments (thick dots)

ionic solutions in the two electrode compartments (fine dots).

The examples 1, 2, 3, 4 and 5 below are provided in illustrative manner to indicate the possible applications of the apparatus of the invention as well as its performance; the examples 6 and 7 illustrate the existence of a separation factor maximum when the thickness of the fractionating chambers is varied while the other parameters are kept constant.

The examples 1 through 5 were translated into practice for an apparatus of the above described type and with the following parameters:

5 fractionating chambers 11 liquid streamlets between the strips of each chamber 60 cm$^2$ of active surface in each membrane each chamber is 3 mm thick the ionic solution in the electrode compartments is of the same nature as the auxiliary solution but with a double saline concentration.

The feed and evacuation rates hereunder are mean rates normalized to the useful width of a membrane and are expressed in cm$^3$/h/cm.

EXAMPLE 1

Fractionating a bovine blood serum to obtain a liquid fraction rich in albumin and in alpha-globulins.

This liquid fraction was obtained by fractionating twice in series in two stages in the apparatus.

Stage 1

The auxiliary solution circulating in the end compartments is a mixture of Na$_2$HPO$_4$-KH$_2$PO$_4$ with a saline concentration $C_T=0.10$ M and a pH of 6.00.

The initial feed solution for the fractionating chambers is pure bovine serum and pH between 7.5 and 8 and of the following composition:

Total protein concentration $C_{o\ total}=75.00$ g/l
albumin: 29% $C_{oA}=21.75$ g/l (initial albumin concentration)
alpha globulins: 13% $C_{o\ alpha}=9.75$ g/l
beta globulins: 13% $C_{o\ beta}=9.75$ g/l
gamma globulins: 45% $C_{o\ gamma}=33.75$ g/l The following operating conditions apply:
d=3.8 cm³/h.cm (initial solution feed rate)
$d_H$=3 cm³/h.cm (evacuation rate from the upper part of the fractionating chambers)
$d_B$=0.8 cm³/h.cm (evacuation rate from the lower part)
$\Delta V_m$=5.50 volts (voltage difference between the two end membranes of the end fractionating chambers)
I=0.98 amp (current through the chambers)

The results obtained in this stage are summarized in the table I below (where Q/Qo is the ratio of the amount of recovered substance in the fraction being considered to the amount present in the initial solution).

It can be seen that the solution from the bottom of the cell contains (49% of albumin and 20% of alpha globulins. The power consumption is 57 watt-hour to treat one liter of initial solution.

TABLE I

| | Evacuation | | | | | |
|---|---|---|---|---|---|---|
| | Bottom | | | Top | | |
| Fraction | Composition % | Concentration g/l | Q/Qo % | Composition % | Concentration g/l | Q/Qo % |
| Albumin | 49 | 98,16 | 95 | 5 | 2,16 | 8 |
| α-globulin | 20 | 40,06 | 86 | 7 | 3,03 | 24 |
| β-globulin | 9 | 18,02 | 39 | 15 | 6,49 | 53 |
| γ-globulin | 23 | 46,07 | 29 | 73 | 31,57 | 74 |
| TOTAL | 100 | 202,31 | | 100 | 43,25 | |

W = 57 Wh/l

Stage 2

The second stage consists in fractionating the liquid fraction collected at the bottom of the chambers during the stage 1. This high concentration (202.31 g/l) fraction is diluted 7 fold before being treated.

Operating Conditions:

auxiliary solution circulating in the end compartments: Na₂HPO₄-KH₂PO₄; $C_T$=0.10 M and pH=6.00 fractionating chamber feed solution: fraction from the bottom of stage 1 (diluted 7-fold in a solution of Na₂HPO₄-KH₂PO₄; $C_T$=0.10 M and pH=6.00) of the following compositions:

$C_{o\ total}$=28.90 g/l
albumin: 49% $C_{oA}$=14.02 g/l
alpha globulins: 20% $C_{o\ alpha}$=5.72 g/l
beta globulins: 9% $C_{o\ beta}$=2.57 g/l
d=3.8 cm³/h.cm
$d_H$=3 cm³/h.cm
$d_B$=0.8 cm³/h.cm
$\Delta V_M$=6.13 volts
I=1.09 amp.

Examination of the table I' below summarizing the obtained results shows that fractions rich in albumine (62%) and in alpha globulins (23%) are obtained. For the whole of these two stages, 70% of the albumin and 58% of the alpha globulins present in the initial solution are recovered in the bottom fractions.

TABLE I'

| | Evacuation | | | | | |
|---|---|---|---|---|---|---|
| | Bottom | | | Top | | |
| Fraction | Composition % | Concentration g/l | Q/Qo % | Composition % | Concentration g/l | Q/Qo % |
| Albumin | 62 | 49,61 | 74 | 30 | 4,51 | 25 |
| α-globulin | 23 | 18,40 | 68 | 12 | 1,76 | 24 |
| β-globulin | 10 | 8,00 | 66 | 9 | 1,32 | 41 |
| γ-globulin | 5 | 4,00 | 13 | 49 | 7,39 | 89 |
| TOTAL | 100 | 80,01 | | 100 | 14,98 | |

W = 70 Wh/l

EXAMPLE 2

Preparing the bovine gamma-globulins.

Operating Conditions auxiliary solution circulating in the end compartments: Na₂HPO₄-KH₂PO₄; pH-6.00 and $C_T$=0.10 M fractionating chambers initial feed solution: pure bovine serum, of the following composition:

$C_{o\ total}$: 73.20 g/l
albumin: 25% $C_{oA}$=18.30 g/l
alpha globulins: 20% $C_{o\ alpha}$=14.64 g/l
beta globulins: 19% $C_{o\ beta}$=13.91 g/l
gamma globulins: 36% $C_{o\ gamma}$=26.35 g/l Biological antitetanus activity T: 400<T<450 I.U./ml d=4.32 cm³/h.cm
$d_H$=dB=2.16 cm³/h.cm
$\Delta Vm$=10.79 volts
I=1.56 amp.

Table II shows that the fraction from the top of the chambers holds only beta and gamma globulins. While the gamma globulin concentration in this fraction (31.10 h/l) is substantially the same as in the initial feed serum (26.35 g/l) of the beta globulins, the concentration in the top fraction (2.70 g/l) is much less than in the initial feed serum (13.91 g/l). The beta-globulins therefore migrate to the anode and this may account for at least in part the loss in biological activity of the top sample (200<T<250 I.U./ml) with respect to initial serum (400<T<450 I.U./ml). Be it noted that 59% of the gamma globulins of the initial solution are recovered at the top of the chambers, the gamma globulins apparently thus migrating slightly to the cathode.

Figure 8:
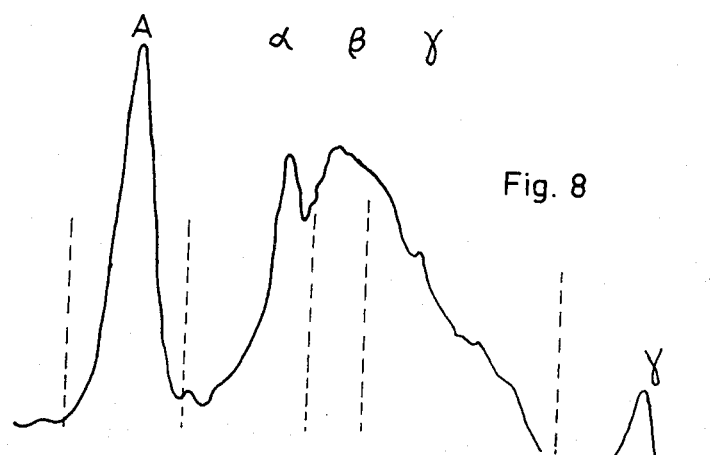
Figure 9:
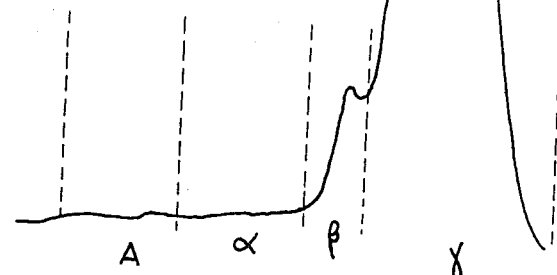

FIGS. 8 and 9 show this example's concentration spectra obtained by analysis on cellulose acetate (IST) for the initial solution (FIG. 8) and for the liquid fraction evacuated from the top (FIG. 9). The strong predominance of the gamma-globulins, a low concentration of the beta-globulins and traces of albumin (A)—the latter not easily distinguished—can be seen.

TABLE II

| | Evacuation | | | | | |
|---|---|---|---|---|---|---|
| | bottom | | | top | | |
| Fraction | Composition % | Concentration g/l | Q/Qo % | Composition % | Concentration g/l | Q/Qo % |
| Albumin | 34 | 37,01 | 101 | 0 | 0 | 0 |

TABLE II-continued

| | Evacuation | | | | | |
|---|---|---|---|---|---|---|
| | bottom | | | top | | |
| Fraction | Composition % | Concentration g/l | Q/Qo % | Composition % | Concentration g/l | Q/Qo % |
| α-globulin | 25 | 28,14 | 96 | 0 | 0 | 0 |
| β-globulin | 22 | 24,05 | 86 | 8 | 2,70 | 10 |
| γ-globulin | 19 | 21,13 | 40 | 92 | 31,10 | 59 |
| TOTAL | 100 | 110,33 | | 100 | 33,80 | |

W = 155 Wh/l
Biological antitetanus activity
"top" 200 < T < 250 I.U./ml

EXAMPLE 3

Preparing bovine beta gama globulins

Operating Conditions the auxiliary solution circulating in the end compartments and the initial feed solution for the fractionating chambers are identical with those of the example 1.

d = 3.8 cm³/h.cm
$d_H$ = 3 cm³/h.cm
$d_B$ = 0.8 cm³/h.cm
$\Delta V_m$ = 4.50 volts
I = 0.89 amps.

Results and Remarks

It can be seen from table III listing the obtained results that the fraction collected at the discharge "top" of the chambers is very rich in beta globulins (35%) and in gamma globulins (44%). The biological activity of this fraction (300<T<400 I.U./ml) clearly exceeds that measured for the top fraction in the example 1 (200<T<250 I.U./ml). This increase may be due to the relatively high concentration of the beta globulins present in the top fraction (13.83 g/l) compared to 13.19 g/l in the initial solution). 78% and 52% resp. of the beta and gamma globulins of the initial feed solution are recovered.

TABLE III

| | Evacuation | | | | | |
|---|---|---|---|---|---|---|
| | bottom | | | top | | |
| Fraction | Composition % | Concentration g/l | Q/Qo % | Composition % | Concentration g/l | Q/Qo % |
| Albumin | 38 | 71,15 | 81 | 7 | 2,77 | 12 |
| α-globulins | 26 | 48,68 | 70 | 14 | 5,53 | 30 |
| β-globulins | 9 | 16,85 | 26 | 35 | 13,83 | 78 |
| γ-globulins | 27 | 40,05 | 40 | 44 | 17,38 | 52 |
| TOTAL | 100 | 187,23 | | 100 | 39,50 | |

W = 42 Wh/l
Biological antitetanus activity
"top" 300 < T < 400 I.U./ml

Figure 10:
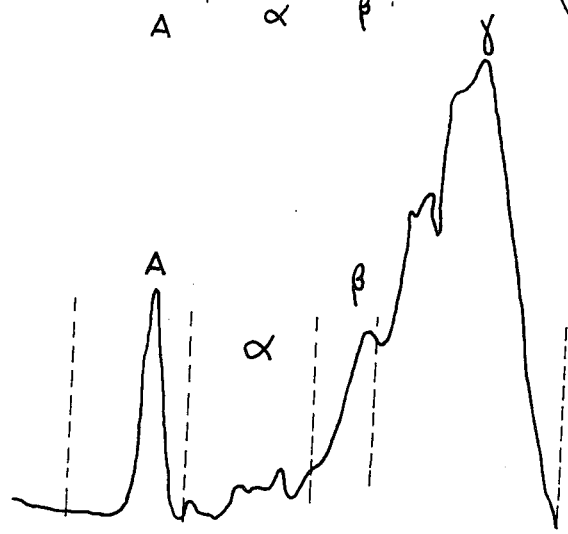

FIG. 10 shows the concentration spectrum of the top fraction and obtained by analysis on cellulose acetate; it indicates the high concentration in gamma and beta globulins, also a trace of albumin.

EXAMPLES 4 and 5

Preparing equine beta-gamma globulins

Operating Conditions auxiliary solution circulating in the end compartments: $Na_2HPO_4$-$KH_2PO_4$; $C_T$=0.10 M; pH=6.00
initial feed solution for the fractionating chambers: pure equine serum of the following composition:
$C_{o\ total}$: 58.60 g/l
albumin: 41% $C_{oA}$=24.03 g/l
alpha globulin: 7% $C_{o\ alpha}$=4.10 g/l
beta-gamma globulin: 52% $C_{o\ beta\text{-}gamma}$=30.47 g/l
Activities in the alpha, beta, epsilon antitoxins and edemations:
alpha: 300 I.U./ml
beta: 300<T<350 I.U./ml
epsilon: 10<T<15 I.U./ml
septic: 10<T<15 I.U./ml
edemations: 25<T<50 I.U./ml

| | | |
|---|---|---|
| d | = 2.4 cm³/h cm | for example 4 |
| $d_H = d_B$ | = 1.2 cm³/h cm | |
| d | = 5.44 cm³/h cm | for example 5 |
| $d_H = d_B$ | = 2.72 cm³/h cm | |
| $\Delta V_m$ | = 9.12 volts | for both examples |
| I | = 1.60 amps | |

Results and Remarks

Figure 11:
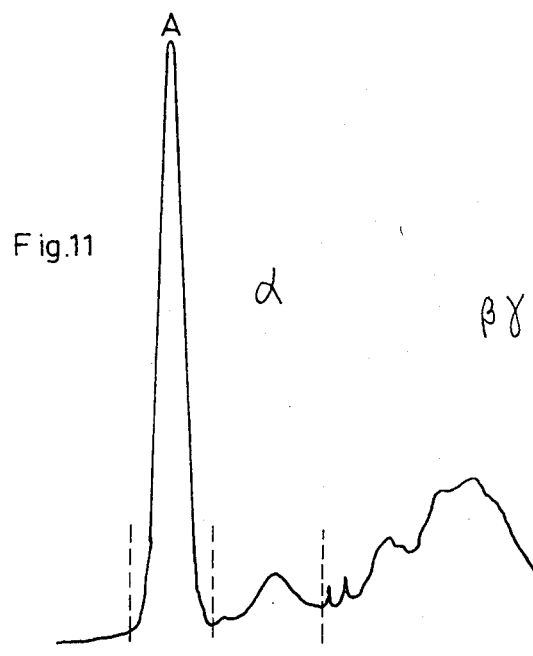
Figure 12:
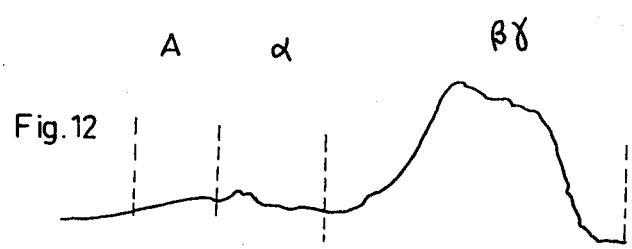
Figure 13:
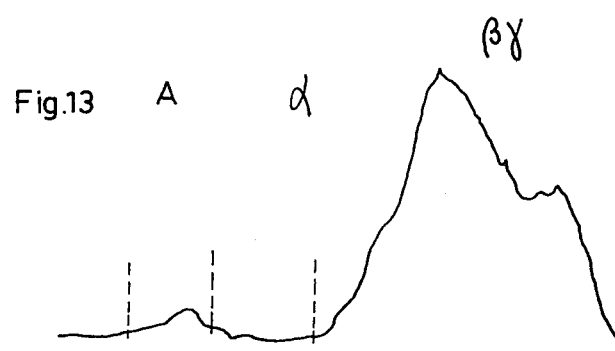

In table IV (example 4) and table V (example 5) summarizing the results obtained, it can be seen that for the two flow rates studied, the liquid fraction flowing from the top of the chambers only contains beta-gamma globulins. However, the highest feed flow rate (5.44 cm³/h.cm) allows obtaining a more concentrated (34.50 g/l) liquid fraction than the lower flow rate (2.4 cm³/h.cm) for which the concentration is lower (21.92 g/l). The concentration in beta-gamma globulins of the top fraction of the example 5 results in relatively high biological activity titers which often are close to the initial feed serum. For those examples, the FIG. 11 shows the initial solution concentration obtained on cellulose acetate; FIG. 12 shows the top liquid fraction concentration obtained from example 4 and FIG. 3 shows the top liquid fraction concentration obtained from the example 5. A slight trace of albumin is noted in the two analyzed samples. Also there is a high concentration in beta globulins in the top fraction from the example 5 and most likely related to the high biological activity of this fraction.

EXAMPLES 6 and 7

The examples were carried out with apparatus of the previously described kind wherein the frame thickness and hence the distance between the membranes were made to vary; in each example, the variation curve of the separation factor has been plotted against the distance between the membranes (FIGS. 14 and 15).

Example 6 was preformed under the following conditions:
the initial solution consists of a 0.3 g/l solution of albumin in a mixture of $Na_2HPO_4$-$KH_2PO_4$ at a concentration of 0.10 M (pH=7);
the auxiliary solution consists of the above cited mixture
feed flow rate: 5.6 cm³/h.cm
top evacuation rate: 2.8 cm³/h.cm bottom evacuation rate: 2.8 cm³/h.cm
electric field: 1 volt/cm.

TABLE IV

| | Evacuation | | | | | |
|---|---|---|---|---|---|---|
| | bottom | | | top | | |
| Fraction | Composition % | Concentration g/l | Q/Qo % | Composition % | Concentration g/l | Q/Qo % |
| Albumin | 50 | 47,50 | 98 | 0 | 0 | 0 |
| α-globulin | 10 | 9,00 | 110 | 0 | 0 | 0 |
| β γ-globulin | 40 | 37,20 | 61 | 100 | 21,92 | 36 |
| TOTAL | 100 | 93,70 | | 100 | 21,92 | |

W = 243 Wh/l
Biological activity "top"
α 150 200
β 150
ε4 < T < 6
Sept 5 < T < 10
Edema 20 < T < 30 I.U./ml
d = 2,4 cm³/h cm

TABLE V

| | Evacuation | | | | | |
|---|---|---|---|---|---|---|
| Fraction | Composition % | Concentration g/l | Q/Qo % | Composition % | Concentration g/l | Q/Qo % |
| Albumin | 57 | 48,20 | 100 | 0 | 0 | 0 |
| α-globulin | 11 | 9,00 | 109 | 0 | 0 | 0 |
| β γ-globulin | 32 | 27,23 | 45 | 100 | 34,59 | 57 |

W = 107 Wh/l
Biological activity "top"
α 200 T 300
β 250
ε 5 < T < 10
Sept 5
Edema 20 < T < 30
d = 5,44 cm³/h cm The curve of FIG. 14 shows that the separation factor (that is the ratio of the bottom fraction albumine concentration to the top fraction albumine concentration) has a sharp maximum for a membrane separation of 0.25 cm.

It is therefore critical in practice to arrange for the conditions of the maximum which depend on the flow rates and the nature of the substances. In each particular case where given substances must be fractionated, the adjustment to obtain optimum conditions can be implemented by fractionating frames with a given thickness (practically between 0.15 and 0.40 cm) and by varying the feed and evacuation rates until falling into the zone of the maximum; in case such flow should be constrained by particular implementation conditions of the application preliminary tests shall be in the lab with apparatus of different frame thickness so as to plot the curve of the separation factor vs this thickness. The final apparatus will be built by selecting the thickness corresponding to the maximum of that curve.

The example 7 was performed under conditions similar to the preceding one but at a different flow rates:
feed rate: 12.8 cm³/h.cm
top evacuation rate: 6.4 cm³/h.cm
bottom evacuation rate: 6.4 cm³/h.cm It is noted that the maximum is as pronounced as before but slightly shifted; in this instance it is obtained for a membrane spacing of 0.3 cm.

We claim:

1. An electrophoretic fractionating apparatus for separating solutions containing dissolved substances, in particular solutions containing proteins, comprising:
   (a) a frame;
   (b) first and second opposed electrodes mounted to said frame and extending therefrom and including means for generating an electric field between said electrodes;
   (c) first and second opposed semi-permeable membranes, each of said membranes being adjacent one of said electrodes;
   (d) a fractionating chamber having first and second parallel surfaces and being of a pre-determined thickness positioned between said membranes;
   (e) solution intake means associated with said chamber;
   (f) solution evacuation means associated with said chamber and at a distance from said intake means;
   (g) said fractionating chamber including a plurality of spaced parallel strips for dividing said chamber into a plurality of compartments of substantially equal volume, said strips having a thickness equal to said chamber thickness adapted for maintaining said membranes said pre-determined thickness apart;
   (h) said solution intake means including a first compartment associated with said first surface and having a depth less than said chamber thickness and spanning said plurality of said strips for distributing said solution to said compartments;
   (i) said solution evacuation means including a second compartment associated with said second surface and having a depth less than said chamber thickness and spanning said plurality of said strips for evacuating said solution; and,
   (j) said chamber having partition elements located on one hand along one side of said chamber to separate said intake means from said evauacation means and on the other hand along the opposite side for the purpose of bounding the evacuation means in the vicinity of the first membrane.

2. An apparatus as in claim 1, further comprising:
   a. said fractionating chamber being comprised of a first and a second panel, said panels being identical and having a thickness one-half of said chamber thickness;
   b. each of said panels having first and second parallel surfaces whereby said first panel first surface abuts said second panel second surface;
   c. each of said panels first surface having said first compartment;
   d. each of said panels second surface having said second compartment; and,
   e. said panels being hermetically sealed.

3. An apparatus as in claim 2, further comprising:
   a. opposed first and second spacer compartments positioned adjacent said first and said second membranes and opposed from said first and said second electrodes and having an internal chamber;
   b. third and fourth opposed semi-permeable membranes positioned adjacent said first and said second spacer compartments and opposed from said first and second membranes;
   c. each of said spacer compartments having auxiliary solution intake means associated with said internal chamber;
   d. each of said spacer compartments having auxiliary solution evacuation means opposed from and a distance from said spacer compartments intake means and associated with said internal chamber; and, e. each of said spacer compartments having a plurality of strips spanning said internal chamber for dividing said chamber into a plurality of substantially equal volumes, each of said plurality of said strips co-planar with a strip of an adjacent fractionating chamber.

4. An apparatus as in claim 1, further comprising:
a. an optimal thickness corresponding to a maximum separation factor based upon said dissolved substances and a desired flow rate; and,
b. said chamber pre-determined thickness being substantially equal to said optimal thickness.

5. An apparatus as in claim 4, wherein:
a. said optimal thickness ranging substantially from 0.15 centimeters to 0.40 centimeters.

6. An apparatus as in claim 1, further comprising:
a. a plurality of said fractionating chambers; and,
b. each of said fractionating chambers being bounded by a pair of semi-permeable membranes.

7. An apparatus as in claim 6, further comprising:
a. said plurality of said fractionating chambers intake means interconnected by co-axial apertures; and,
b. said plurality of said fractionating chambers evacuation means interconnected by co-axial apertures.

8. An apparatus as in claim 1, further comprising:
a. first and second opposed partition elements;
b. said first partition element being associated with said intake means and said second surface of said chamber; and,
c. said second partition element being associated with said evacuation means and said first surface of said chamber.

9. An apparatus as in claim 8, further comprising:
a. said partition elements comprising a longitudinally extending member having first and second parallel surfaces;
b. said second surface of said partition elements having a length greater than said first surface of said partition elements; and,
c. said partition elements having an angled portion connecting said first and said second partition surfaces.

10. An electrophoretic fractionating apparatus for separating solutions containing dissolved substances, in particular solutions containing proteins, comprising:
(a) electrodes for generating an electric field and including between them at least two semi-permeable membranes defining at least one fractionating chamber provided with solution intake means and liquid fraction evacuation means;
(b) said at least one fractionating chamber being bounded by a peripheral frame having a plurality of strips defining two sides of said frame and being of the same thickness as said frame;
(c) said two-semi-permeable membranes being applied on either side against the faces of said frame and against the faces of said strips so that said membranes are kept in place and apart by a constant distance across their entire surface and in that the volume included between said membranes is divided by said strips into a plurality of elongated volumes;
(d) said solution intake means and said fraction evacuation means in said at least one fractionating chamber includes conduits fashioned along the two sides of said frame that are joined by the strips;
(e) said elongated volumes separated by said strips extending between said conduits so that said supply toward said volumes as well as the evacuation from them be implemented in parallel through said conduits; and,
(f) said at least one fractionating chamber having partition elements located on one hand along one side of said frame to separate said intake conduit from said evacuation conduit and on the other hand along the opposite side for the purpose of bounding the evauaction conduit in the vicinity of the first membrane.

* * * * *